United States Patent [19]

Riou et al.

[11] Patent Number: 4,482,378
[45] Date of Patent: Nov. 13, 1984

[54] COLOR DEVELOPERS AND THERMOGRAPHIC RECORD COMPOSITIONS CONTAINING THEM

[75] Inventors: Claude R. Riou, Veyrier du Lac; Jean F. Fayard, Cran-Gevrier, both of France

[73] Assignee: Societe Anonyme: Aussedat-Rey, France

[21] Appl. No.: 388,690

[22] Filed: Jun. 15, 1982

[30] Foreign Application Priority Data

Jun. 24, 1981 [FR] France ................................. 81 12910

[51] Int. Cl.³ .................... B41M 5/18; B41M 5/22; C09D 11/00
[52] U.S. Cl. ................................. 106/14.5; 106/21; 106/22; 106/23; 106/31; 427/151; 346/210; 346/211; 346/212; 346/216; 346/217; 346/225
[58] Field of Search ................. 106/14.5, 21, 31, 19, 106/20, 22, 23; 282/27.5; 428/320.6, 320.8, 411, 488, 537, 913, 914; 427/150–153

[56] References Cited

U.S. PATENT DOCUMENTS

| | | | |
|---|---|---|---|
| 3,413,138 | 11/1968 | Georgalas et al. | 282/27.5 |
| 3,539,375 | 11/1970 | Baum et al. | 282/27.5 |
| 3,746,675 | 7/1973 | Blose et al. | 282/27.5 |

FOREIGN PATENT DOCUMENTS

| | | | |
|---|---|---|---|
| 1296048 | 5/1962 | France | 282/27.5 |
| 1440892 | 4/1966 | France | 282/27.5 |
| 2272082 | 12/1975 | France | 282/27.5 |
| 2391858 | 12/1978 | France | 282/27.5 |
| 2427210 | 12/1979 | France | 282/27.5 |
| 2427209 | 12/1979 | France | 282/27.5 |
| 2442139 | 6/1980 | France | 282/27.5 |
| 53-023205 | 7/1978 | Japan | 282/27.5 |
| 0104908 | 8/1979 | Japan | 428/320.6 |
| 55-55891 | 4/1980 | Japan | 282/27.5 |
| 406257 | 8/1966 | Switzerland | 282/27.5 |
| 2044284 | 10/1980 | United Kingdom | 282/27.5 |

OTHER PUBLICATIONS

V. Grignand, et al., "Traite de Chimie Organique," Tome XXI, 1953, Chapter: Benzothiazoles Vicinaux, pp. 737–785.

Curtis, "Quantitative Determination and Separation of Copper with Benzotriazole," *Industrial and Engineering Chemistry*, Analytical Edition, vol. 13, No. 5, May 15, 1941.

Benson, et al., "The Chemistry of Vicinal Triazoles," *Chemical Reviews*, vol. 46, (1950), pp. 1–7, 38–51, and 62–65.

*Primary Examiner*—Bruce H. Hess
*Attorney, Agent, or Firm*—Lerner, David, Littenberg, Krumholz & Mentlik

[57] ABSTRACT

The present invention relates to thermographic record compositions and to novel color developers for thermographic compositions consisting of:
the compounds of formula:

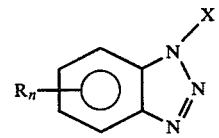

in which R represents: H, alkyl, $NO_2$, halogen, aryl, $NH_2$, OH, COOH, $HSO_3$, $NR_1R_2$, $COOR_3$, $OR_4$ ($R_1$, $R_2$, $R_3$, $R_4$ = alkyl or aryl), X represents H or a group possessing a labile H capable of forming a stable anion by loss of a proton $H^+$,
or their salts of formula, when X=H:

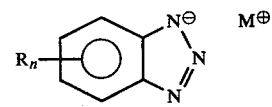

in which R and n are as defined hereinabove and $M^+$ represents a metal cation. The invention is more particularly applicable to supports for recording data.

24 Claims, No Drawings

COLOR DEVELOPERS AND THERMOGRAPHIC RECORD COMPOSITIONS CONTAINING THEM

The present invention relates to novel thermographic record compositions as well as to the thermographic record supports obtained from these compositions. The invention is characterised by the use of derivatives of benzotriazole of formula:

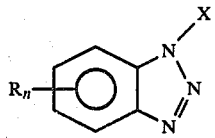

or their salts when $X=H$ $0 \leq n \leq 4$

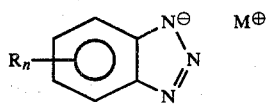

the substituent or substituents R of the benzene part, which are identical or different, being the following: H, alkyl, $NO_2$, halogen, aryl, $NH_2$, OH, COOH, $HSO_3$, $NR_1R_2$, $COOR_3, OR_4$ ($R_1$, $R_2$, $R_3$, $R_4$=alkyl or aryl, X representing H or a group possessing a labile H and capable of forming a stable anion by loss of a proton $H^+$, and $M^+$ representing a metal cation), or mixtures thereof, as colour developer in thermoreactive compositions comprising a colour former compound. Preferably, X represents H, —OH, $(CH_2)_m$—OH, with $1 \leq m \leq 10$, or

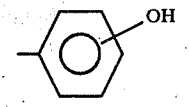

the hydrogen atom being particularly preferred. Upon a rise in temperature, these derivatives of benzotriazole or their salts react with the colour former to give an irreversible coloration. These two types of products are conditioned on a support (paper or the like) which may be used in all apparatus having a thermic data display system: for example calculator printers, medical and industrial surveillance apparatus, telecopiers, . . . .

At the present time, industrial uses of benzotriazole and its derivatives are as follows:

additive used in small quantities as anti-corrosion agent (mainly copper) in anti-freeze products and refrigerating brines; for this application, benzotriazole is especially used;

in photography, benzotriazole and its derivatives are used as fog-inhibitor; they also act as development retarder; these effects are probably obtained by a reaction with the silver halide present in the photographic film;

in photography and also in the polymer and plastic industry, the derivatives of benzotriazole are used as anti-UV. The N-substituted derivatives of benzotriazole are, in this case, mainly used, for example Tinuvin 328 of formula

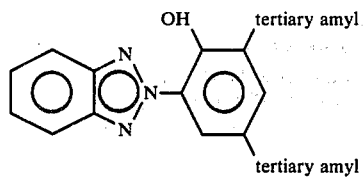

marketed by CIBA-GEIGY. These products absorb the radiations in the near ultra-violet (300 to 400 nm) and thus product from these radiations the materials which contain them.

None of these uses have anything to do with the use forming the subject matter of the invention: developer of colour formers in thermoreactive compositions.

The recent increase in the information and communication needs has increased the use and demand for data recording, transmission and retrieving systems. Among these systems, thermoreactive systems have made great strides, for several reasons: the process of forming the image is simple and enables good quality reproductions as regards colour and contrast to be obtained, the apparatus used are often easy to maintain and to use, the thermal record sheet, in addition to its remarkable technical performances, is of relatively low cost.

Heat sensitive copy sheets which may be used for these applications are initially known from French Pat. No. 1 440 892 (National Cash Register Company) and thereafter in the cascade of Patents deriving from this main system, for example U.S. Pat. Nos. 3,539,375 and 3,746,675, both to the NCR Company.

All these patents relate to the following system: heating induces the reaction in the molten state of a colourless or pale chromogenic leuco-colorant (colour former) and of a phenolic substance (developer) and leads to the formation of a coloured species.

Different leuco-colorant-phenolic compound couples have been described for these thermographic applications; for the former, mention may be made of: indolinic spiropyrans, triphenyl-methane colorant lactones, compounds of the family of fluorans, phthalides, spirodihydropyrans(French Pat. No. 2 272 082), chromenes or chromanes . . . . For the latter, mention may be made of: bisphenol A (isopropylidene-4,4' diphenol), p-tertiobutylphenol, p-phenylphenol, p,p'-(methyl-1-n-hexylidene) diphenol, phenolic novolac resins . . . .

Thermoreactive record compositions are also known which contain other developers of the leuco-colorants described above, in place of the phenolic compounds, such as for example:

metal salts of organic and preferably fatty acids (resinates, acetates, phenates, stearates, ricinoleates, oleates . . . ). Swiss Pat. No. 406 257 (NCR Company).

compounds of structure

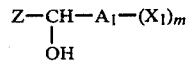

French Patent Application No. 79 28857 (CIBA GEIGY A.G.).

carbonates or ethers derived from dihydroxy-2,3-naphthalene. French Patent Appln. No. 2 427 210 (78 16954) (LA CELLOPHANE).

silicon and phosphorus derivatives of dihydroxy-2,3-naphthalene. French Patent Appln. No. 2 427 209 (78 16953) (LA CELLOPHANE).

electronegatively substituted monoaldehydes or polyaldehydes and/or their products of reaction with an organic compound containing hydroxyl groups or the intermediate products. French Patent Appln. No. 2 391 858 (78 15806) (CIBA-GEIGY A.G.).

All these process have, of course, their own qualities; nevertheless, most of them have imperfections, particularly concerning the long-term stability and persistence of the recorded image; in fact, the majority of them present a more or less marked reduction of the colorations recorded under the effect of the ambient light, as well as an increase of the background fog under the effect of humidity and heat.

This stability of the recorded image and of the uncoloured background depends, of course, on the nature and structure of the leuco-colorant colour generator used, but also on the developer chosen in combination therewith. The combination chosen between the colorant precursor and the developer therefore has considerable influence on the qualities of conservation of the paper and of the image recorded.

It has been discovered according to the invention that, in thermoreactive compositions, a completely different family of compounds could be used as developer in association with conventional colorant precursors.

This family is constituted by the derivatives of benzotriazole of structure

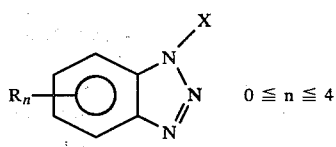

the substituent or substituents R, identical or different, being H, alkyl, aryl, $NO_2$, halogen, $NH_2$, OH, COOH, $NR_1R_2$ ($R_1$, $R_2$=alkyl or aryl), $COOR_3$ ($R_3$=alkyl or aryl), $OR_4$ ($R_4$=alkyl or aryl), $HSO_3$ and X preferably representing H, —OH, $(CH_2)_m$—OH with $1 \leq m \leq 10$, or

As non-limiting examples, mention may be made of benzotriazole, methyl-5 benzotriazole, methyl-6-benzotriazole, phenyl-5 benzatriazole, phenyl-6 benzotriazole, chloro-5 benzotriazole, chloro-5 methyl-6 benzotriazole, chloro-5 isopropyl-7 methyl-4 benzotriazole, bromo-5 benzotriazole, nitro-4 (or 7) benzotriazole, nitro-5 (or 6) benzotriazole, nitro-5 dimethyl-4,7 benzotriazole, dinitro-4,6 (or 5,7) benzotriazole, amino-4 (or 7) benzotriazole, amino-5 (or 6) benzo triazole, amino-5 (or 6) methyl-6 (or 5) benzotriazole, amino-5 (or 6) methyl-7 (or 4) benzotriazole, amino-5 (or 6) dimethyl-4,7 benzotriazole, amino-5 chloro-4 benzotriazole, amino-4 hydroxy-7 benzotriazole, amino-7 carboxy-5 benzotriazole, diamino-4,5 (or 6,7) benzotriazole, hydroxy-4 (or 7) benzotriazole, hydroxy-5 (or 6) benzotriazole, diethoxy-4,7 benzotriazole, dihydroxy-4,5 benzotriazolyl-7 sulfonic acid, acetyl-5 benzotriazole, benzotriazolecarboxylic-5 (or 6) acid and analogous compounds.

More ample information on these compounds as chemical products may be obtained in the following publications:

Traité de Chimie Organique by V. GRIGNARD, vol. XXI, page 737 et seq.

F. BENSON and W. SAVELL, Chemical Reviews, 1950, 46, 1–68.

These compounds, non N-substituted derivatives of benzotriazole, are used according to the invention either as such or in the form of salts.

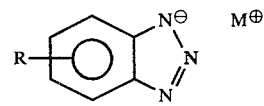

These salts are obtained by direct reaction of the derivative of benzotriazole with an adequate metal salt. The metal salts leading most easily to benzotriazole complexes are the salts of the following metals: Cu, Cd, Co, Fe (II), Ni Mn, Zn.

The following can be mentioned as literature concerning the metal salts of benzotriazole as chemical products:

J. A. CURTIS, Ind. Eng. Chem. Anal. Ed., 1941, 13, 349.

J. E. FAGEL and G. W. EWING, J. Am. Chem. Soc. 73, 4360 (1951).

The thermographic record compositions according to the invention therefore contain the following constituents: one or more colour formers: this product may belong to various chemical families conventionally used in thermoreaction such as for example triphenyl methane colorant lactones, fluorans, phthalides, triaryl methane leuco-colorants, spiropyrans, chromenes, chromanes, substituted phenothiazine or phenoxazine leucocolorants. The following compounds may be mentioned by way of non-limiting example as colour formers:

3,3-bis (p-dimethylaminophenyl)-6-dimethylaminophthalide (CVL), 3,3-bis-(p-dimethylaminophenyl) phthalide, 3-(p-dimethylaminophenyl)-3-(1,2-dimethylindole-3-yl) phthalide, 3-(p-dimethylaminophenyl)-3-(2-methylindole-3-yl)phthalide, 3,3-bis-(1,2-dimethylindole-3-yl)-5-dimethylaminophthalide, 3,3-bis-(1,2-dimethylindole-3-yl)-6-dimethylaminophthalide, 3,3-bis-(9-ethylcarbazole-3-yl)-5-dimethyl aminophthalide, 3,3-bis (2-phenylindole-3-yl)-5-dimethylaminophthalide, 3-p-dimethylaminophenyl-3-(1-methylpyrrole-2-yl)-6-dimethylaminophthalide, benzyl ether of 4,4'-bis-dimethylaminobenzhydrine, N-halophenyl-leuco-auramine, N-2,4,5-trichlorophenyl-leuco-auramine, rhodamine-B-anilinolactame, rhodamine-(p-nitro-anilino) lactame, rhodamine-(p-chloroanilino) lactame, 7-dimethyl-amino-2-methoxyfluoran, 7-diethylamino-2-methoxyfluoran, 7-diethylamino-3-methoxyfluoran, 7-diethylamino-3-chlorofluoran, 7-diethylamino-3-chloro-2-methylfluoran, 7-diethylamino-2, 3-dimethylfluoran, 7-diethylamino-(3-acetylmethylamino)fluoran, 7-diethylamino-(3-methylamino)fluorane, 3,7-diethylaminofluoran, 7-diethylamino-3-(dibenzylamino)fluoran, 7-diethylamino-3-(methylbenzylamino)fluoran, 7-diethylamino-3-(chlorethylmethyl-amino)fluoran, 7-diethylamino-3-(diathylamino)fluorane, 2-phenylamino-3-methyl-6-(N-ethyl-N-p-toluyl)amino-fluoran, benzoyl-leucomethylene blue, p-nitrobenzyl-leucomethylene blue, 3-methyl-spiro-dinaphthopyran, 3-ethyl-spiro-dinaphthopyran, 3,3'-dichloro-spiro-dinaphthopyran, 3-benzyl-spiro-dinaphthopyran, 3-methyl-naphtho-(3-methoxybenzo)-spiro-pyran and 3-propyl-spiro-dibenzopyran.

The colourless chromogenic substances mentioned above may be used individually or in mixture.

The benzotriazoles used according to the invention make it possible optimally to develop all the known colour formers. This development is optimal taking into account the colour former used. However, a certain number of qualities of the print formed: colour, stability, intensity . . . depend mainly on the nature of the colour former and in particular on the chemical structure of the family to which it belongs. In the present case, the colour developer of the benzotriazole family reinforces certain of these qualities: intensity, stability with respect to light, to humidity, but does not modify them radically; thus for example a colour former leading, by the action of a conventional colour developer, to a colorant not very stable under the effect of light, will, by the use of derivatives of benzotriazole, have its behaviour with respect to the light slightly improved, but it will still not become excellent.

a colour developer, characteristic of the invention, belonging to the family of the derivatives of benzotriazole:

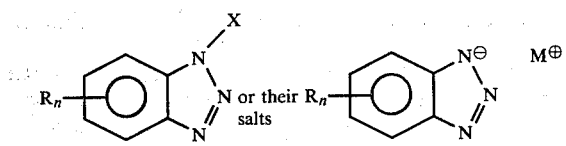

as defined previously.

These compositions further contain all the species necessary for forming a good quality coat on the support.

a polymer binder, of which the principal role is to ensure cohesion of all of the emulsion, as well as its attachment to the support; it may also intervene by its inherent characteristics on the softening of the coat. These binders are either water-soluble (the colour generator and the developer being insoluble or very sparingly soluble in water), in which case there may be one coat, or soluble in organic solvents, in which case it is better to have two coats when the solvent used renders soluble the colour former or the developer to avoid any premature reaction between these two compounds. The colour former and the developer are then placed in different coats. These binders may be selected from the following families: acrylic, vinyl, cellulosic, styrene, halogen, maleic . . . latices or polymers. Mention may be made, as non-limiting examples, of: starch, polyvinyl alcohol, hydroxyethyl cellulose, methyl cellulose, carboxy-methyl cellulose, gelatin, casein, gum arabic, styrene and maleic anhydride copolymer salts, an emulsion of a styrene and butadiene copolymer, an emulsion of a vinyl acetate and maleic anhydride copolymer, a copolymer of vinylidene chloride . . .

waxes or compounds with low melting point which serve to adjust the temperature of reaction of the medium to a desired value, to prevent adhesion to the heating head, to avoid soiling by friction; for example, paraffinic waxes, polyolefinic waxes, fatty amides and their derivatives of methylol, higher fatty acids and their metal salts, the products of condensation of a higher fatty acid and of an amine, esters of polyalcohols and of higher fatty acids, higher alcohols . . .

a pigmentary filler adapted to give a better consistency to the coating composition, to improve the whiteness of the background, to reduce the problems of tackiness of the coat and the phenomena of fouling and wear of the apparatus using these emulsions; for example, $CaCO_3$, kaolin, talc, starch, $TiO_2$, ZnO, $MgCO_3$, $Al(OH)_3$, calcined clay, organic pigments such as urea-formaldehyde polymerisates (for example, "Pergopak" of CIBA-GEIGY).

different adjuvants currently used for the preparation and coating of the emulsions: dispersants, bluing agents, surface-active agents, anti-foaming agents, plasticizers, anti-oxidants, anti-UV, agents buffering the pH of the medium and stabilising the composition such as $NaHCO_3$ or $NH_4HCO_3$. The choice and nature of each of these products is easily made by a man skilled in the art.

All these different constituents are milled, emulsified or dissolved in the medium and coated in one or more coats on a paper or other (e.g. plastic) support. The colour former and the colour developer are preferably milled separately so as to avoid any premature reaction; the two dispersions being mixed before coating in the case of one coating being made. The nature, weight per surface unit and the number and thickness of the coats and their mode of coating depend on the use provided, as well as on the desired effect, and are easily determined by a man skilled in the art.

The following different examples are given by way of illustration and are in no way limiting.

EXAMPLE 1

The following compositions are milled separately:

|   |   |   | dry weight | % dry |
|---|---|---|---|---|
| 1 | 5% polyvinyl alcohol in water Rhodoviol 4-20 (RHONE-POULENC) | 87 g | 4.4 g | 25.3 |
|   | Benzotriazole | 9 g | 9 | 51.7 |
|   | Kaolin Ultra White 90 (ENGELHARDT) | 3.5 g | 3.5 | 20.1 |
|   | Kemamide S (Stearamide of HUMKO Chemical) | 0.4 g | 0.4 | 2.3 |
|   | Anti-foam T of BAYER | 0.1 g | 0.1 | 0.6 |
|   |   |   | 17,4 g | 100,0 |
| 2 | Crystal Violet lactone (Reakt Violet K of BASF) | 1.6 g | 1.6 |   |
|   | 1% hydroxyethyl cellulose in water Cellocize QP 40 L (UNION CARBIDE) | 80.0 g | 0.8 |   |
|   | Kemamide S | 1.5 g | 1.5 |   |
|   | Lissapol N (surface-active agent of ICI) | 0.1 g | 0.1 |   |
|   | Anti-foam T of BAYER | 0.1 g | 0.1 |   |

| | dry weight | % dry |
|---|---|---|
| | 4.1 g | |

These two compositions are mixed in the ratio 1/1, then coated on a paper of 55 g/m² in a proportion of 5 g/m² dry. After drying and possible calendering, this paper is used on an OLIVETTI Logos No. 7 office calculating machine with thermo printer; the blue print has a density of 1.1 (measured with the aid of a density-meter GAM RD 144 equipped with a Wratten filter No. 106); the reaction threshold of the paper is very marked and is situated at about 85° C.

EXAMPLE 2

The following composition is dispersed homogeneously:

| | | | dry |
|---|---|---|---|
| Coat 1 | Polyvinyl alcohol RHODOVIOL 30-5 with 5% H₂O (produced by RHONE-POULENC) | 60.0 g | 3.0 g |
| | Benzotriazole | 4.5 g | 4.5 g |
| | Kaolin Ultra White 90 | 2.0 g | 2.0 g |
| | Nopco 81-34 (Anti-foam of DOITTAU) | 0.1 g | 0.1 g |
| | | 66.6 g | 9.6 g | this coat is deposited in a proportion of 5 g/m² on a paper support of 55 g/m², then the following composition is deposited thereon, in the proportion of about 1 g/m² dry:

| | | | dry |
|---|---|---|---|
| Coat 2 | NH₄HCO₃ | 3 g | 3 g |
| | Black Colour former PERGASCRIPT-IBR (product of CIBA-GEIGY) | 2 g | 2 g |
| | Kemamide S (amide wax of HUMKO Chemicals | 3 g | 3 g |
| | 1% hydroxyethycellulose in water Cellocize QP 300 L (product of BP Chemical) | 97 g | 0.97 g |
| | Nopco 81-34 (anti-foam) | 0.1 g | 0.1 g |
| | Protesol DOS (spreading agent of PROTEX) | 0.1 g | 0.1 g |
| | | 105.2 g | 9.17 g |

After drying and possible calendering, this paper is used in an apparatus for recording electrocardiograms of the "Cardiopan 571" type by PHILIPS and makes it possible to obtain a very finely resolved black line, whatever the speed of advance of the paper 50, 25 or 10 mm/s. The density of the print is 1.15 (measured with the aid of a density-meter GAM RD 144 equipped with a Wratten filter No. 106).

EXAMPLE 3

Composition identical to Example 2, except that the following is added in the coat 1:
ZnCl₂: 2.6 g
which makes it possible to intensify the thermically obtained black prints (D=1.25) and to improve the characteristics thereof further; in particular, a remarkable stability under the effect of light is obtained; in this way, after exposure for 30 hours in an accelerated ageing apparatus SUNTEST 7011 of HANAU (illumination 90,000 lux), the density of print passed from 1.25 to 1.15; the background passed from 0.08 to 0.120.

EXAMPLE 4

The following composition is dispersed in homogeneous manner;

| | | | dry % |
|---|---|---|---|
| 20% Pliolite VTAC-L (vinyltoluene-acrylate copolymer sold by GOOD YEAR) in essence Exsol DSP 100-130 (ESSO CHIMIE) | 60.0 g | 12.0 g | 19.2 |
| Benzotriazole | 18.0 g | 18.0 g | 28.9 |
| ZnCl₂ | 10.4 g | 10.4 g | 16.7 |
| Kaolin Ultra White 90 | 8.0 g | 8.0 g | 12.8 |
| Black Colour-former Pergascript IBR (CIBA-GEIGY) | 6.0 g | 6.0 g | 9.6 |
| Kemamide S | 8.0 g | 8.0 g | 12.8 |
| Montanox 80 (spreading agent of SEPPIC | 0.1 g | 0.1 g | |
| | 110.5 g | 62.5 g | |

On the hand the benzotriazole+ZnCl₂, and on the other hand the black colour former are milled separately, then mixed before coating, the other constitutents being distributed equitably between the two millings. This coat is deposited in the proportion of 5 g/m² on a polyester support of 100μ thickness; after drying and possible calendering, this thermoreactive film is tested on a "THERMOTEST" apparatus of the firm SETARAM (LYON). Coloration densities of 1.20 (reflection) (Density-meter GAM RD 144, Wratten filter No. 106) and a very marked reaction threshold at about 85° C. are obtained.

EXAMPLE 5

The following compositions are milled homogeneously:

| | | |
|---|---|---|
| Coat 1 | Ixan SGA (vinylidene polychloride produced by SOLVAY) | 27.3 g |
| | Ethyl acetate | 110.0 g |
| | Benzotriazole | 40.9 g |
| | ZnCl₂ | 22.7 g |
| | Kemamide S | 4.0 g |
| | Kemamide E | 5.1 g |

This coat is deposited in a proportion of 5 g/m² dry on a paper support of 55 g/m², then, after drying, the following composition is deposited thereon, in a proportion of about 1 g/m² dry:

| | | |
|---|---|---|
| Coat 2 | Black colour former Pergascript IBR | 20.0 g |
| | Polyvinyl alcohol Rhodoviol 4-20 | 10.0 g |
| | Water | 60.0 g |
| | Kemamide S | 30.0 g |
| | Etingal L (anti-foam of BASF) | 0.1 g |
| | Protesol DOS (spreading agent of PROTEX) | 0.1 g |
| | NH₄HCO₃ (stabilizing agent) | 30.0 g |

After drying and possible calendering, this thermoreactive paper is used on a CANON FAX 601 W telecopier; at high speed, densities of black of 0.90 are obtained and at slow speed, densities of 1.0. The threshold of reactivity of this type of paper is at about 75° C.

EXAMPLE 6

The following compositions are milled homogeneously:

| | | |
|---|---|---|
| Coat 1 | 5% polyvinyl alcohol in water Rhodoviol 4-20 (produced by RHONE-POULENC) | 60.0 g |
| | Benzotriazole | 4.5 g |
| | $ZnCl_2$ | 2.6 g |
| | Kaolin Ultra-White 90 | 2.0 g |
| | Etingal L (anti-foam of BASF) | 0.1 g |

This coat is deposited in a proportion of 5 g/m² dry on a paper support of about 55 g/m²; the following composition is then coated thereon, in a proportion of about 1 g/m² dry:

| | | |
|---|---|---|
| Coat 2 | Crystal Violet lactone colour former (Reakt Violet K of BASF | 6.0 g |
| | Kemamide S | 5.0 g |
| | 20% Pliolite VTAC-L (copolymer of GOOD YEAR) in essence Exsol DSP 100–130 (ESSO CHIMIE) | 60.0 g |
| | Montanox 80 (spreading agent by SEPPIC) | 0.2 g |

After drying and possible calendering, this paper used on an ANDERSON-JACOBSON AJ 630 thermo printer (heating head with matrix of points 5×8) (10 characters per inch and 6 lines per inch), makes it possible to obtain blue recordings with a density of 0.95 to 0.80 depending on the speed selected: 10, 15 or 30 characters per second (density-meter GAM RD 144 with Wratten filter No. 106). The reaction threshold of the paper is marked and is at about 85° C.

EXAMPLE 7

The following compositions are dispersed homogeneously.

| | | | dry |
|---|---|---|---|
| Coat 1 | 5% polyvinyl alcohol Rhodoviol 30-5 (RHONE-POULENC) in water | 60.0 g | 3.0 g |
| | benzotriazole | 4.5 g | 4.5 g |
| | Kaolin Ultra White 90 | 2.0 g | 2.0 g |
| | $Mn(NO_3)_2$ | 3.0 g | 3.0 g |
| | Etingal L (anti-foam) | 0.1 g | |

This coat is deposited in a proportion of 5 g/m² dry on a paper support of 55 g/m²; the following composition is then coated thereon, in a proportion of about 1 g/m² dry:

| | | |
|---|---|---|
| Coat 2 | product T | 2.0 g |
| | Glycerol monostearate | 3.0 g |
| | 1% hydroxyethylcellulose in water Cellocize QP 300 L (BP Chemical) | 97.0 g |
| | Etingal L | 0.1 g |
| | Protesol DOS | 0.1 g |

After drying and possible calendering, this paper is used in an apparatus for recording electrocardiograms, of the "Cardiopan 571" type by PHILIPS, and makes it possible to obtain a red-brown line of density 0.80 (density-meter GAM RD 144 with Wratten filter No. 106).

EXAMPLE 8

The following compositions are dispersed homogeneously:

| | | |
|---|---|---|
| Coat 1 | Ixan SGA | 27.3 g |
| | Ethyl acetate | 110.0 g |
| | Benzotriazole | 40.9 g |
| | $CuSO_4$ | 25.0 g |
| | Kemamide S | 9.1 g |

This coat is deposited in a proportion of about 5 g/m² dry on a paper support of about 55 g/m², then, after drying, the following composition is deposited thereon, in a proportion of about 1 g/m² dry:

| | | |
|---|---|---|
| Coat 2 | Red colour former Pergascript 16-B (CIBA-GEIGY) | 20.0 g |
| | polyvinyl alcohol Rhodoviol 4-20 | 10.0 g |
| | Water | 60.0 g |
| | Kemamide S | 30.0 g |
| | Etingal L | 0.1 g |
| | Protesol DOS | 0.1 g |

After drying and possible calendering, this paper is used on an OLIVETTI Logos No. 7 office calculating machine with thermo printer; the red print has a density of 1.4 (Density-meter GAM RD 144 with green Wratten filter No. 581). The reaction threshold of this type of paper is marked and is at about 80° C. The ratios of the different compounds described in these examples may of course be modified as a function of the required characteristics (sensitivity, conservation, contrast, colour) for the thermo record support, without departing from the scope of the invention.

EXAMPLE 9

This example is identical to Example 5, but the Benzotriazole (40.9 g) is replaced in coat 1 by:
Methyl-6 benzotriazole: 45.7 g
The results obtained with such a paper are virtually identical to those obtained in Example 5.

EXAMPLE 10

The following compositions are milled homogeneously:

| | | |
|---|---|---|
| Coat 1 | Ixan SGA (Vinylidene polychloride produced by SOLVAY) | 27.3 g |
| | ethyl acetate | 110.0 g |
| | chloro-5 benzotriazole | 52.8 g |
| | ZnCl$_2$ | 22.7 g |
| | Kemamide S | 9.1 g |

This coat is deposited in a proportion of 5 g/m$^2$ dry on a paper support of about 55 g/m$^2$, then, after drying, the following composition is deposited thereon, in a proportion of about 1 g/m$^2$ dry:

| | | |
|---|---|---|
| Coat 2 | Colour former Copikem XI (produced and sold by HILTON DAVIS USA) | 20.0 g |
| | polyvinyl alcohol Rhodoviol 4-20 | 10.0 g |
| | Water | 60.0 g |
| | Kemamide S | 30.0 g |
| | Etingal L (anti-foam of BASF) | 0.1 g |
| | Protesol DOS (spreading agent PROTEX) | 0.1 g |
| | NH$_4$HCO$_3$ | 30.0 g |

After drying and possible calendering, this thermoreactive paper is tested on a THERMOTEST apparatus of the firm SETARAM (LYON); coloration densities (orangey-yellow) of 1.4 are obtained (Density meter GAM RD 144 with blue Wratten filter No. 47); the reaction threshold of these thermoreactive papers is at around 95° C.

EXAMPLE 11

The following compositions are milled homogeneously:

| | | |
|---|---|---|
| Coat 1 | Ixan SGA | 27.3 g |
| | ethyl acetate | 110.0 g |
| | dimethyl-5,6 benzotriazole-1H monohydrate | 56.7 g |
| | ZnCl$_2$ | 22.7 g |
| | Kemamide S | 9.1 g |

This coat is deposited in a proportion of 5 g/m$^2$ dry on a paper support of about 55 g/m$^2$; then, after drying, the following composition is deposited thereon in a proportion of about 1 g/m$^2$ dry:

| | | |
|---|---|---|
| Coat 2 | Olive colour former Pergascript IG (CIBA-GEIGY) | 20.0 g |
| | polyvinyl alcohol Rhodoviol 4-20 | 10.0 g |
| | Water | 60.0 g |
| | Kemamide S | 30.0 g |
| | Etingal L | 0.1 g |
| | Protesol DOS | 0.1 g |
| | NH$_4$HCO$_3$ | 30.0 g |

After drying and possibly calendering, this thermoreactive paper is tested on a THERMOTEST apparatus of the firm SETARAM (LYON); coloration densities (olive green) of 1.2 are obtained (Densitymeter GAM RD 144—Wratten filter No. 106). The reaction threshold is at about 85° C.

EXAMPLE 12

The following compositions are homogeneously milled:

| | | |
|---|---|---|
| Coat 1 | Ixan SGA | 27.3 g |
| | ethyl acetate | 110.0 g |
| | nitro-5 benzotriazole | 56.4 g |
| | ZnCl$_2$ | 22.7 g |
| | Kemamide S | 4.1 g |
| | Kemamide E | 5.0 g |

This coat is deposited in a proportion of 5 g/m$^2$ dry on a paper support of about 55 g/m$^2$; then, after drying, the following composition is deposited thereon in a proportion of about 1 g/m$^2$ dry:

| | | |
|---|---|---|
| Coat 2 | black colour former Pergascript IBR | 20.0 g |
| | Polyvinyl alcohol Rhodoviol 4-20 | 8.0 g |
| | Latex Acronal 720 D (BASF) (50% dry matter) | 4.0 g |
| | water | 60.0 g |
| | Kemamide S | 30.0 g |
| | Etingal L | 0.1 g |
| | Protesol DOS | 0.1 g |
| | NH$_4$HCO$_3$ | 30.0 g |

After drying and possible calendering, this thermoreactive paper is tested on an ANDERSON-JACOBSON AJ 630 thermo printer (heating head with matrix of points 5×8); black records of density of 1.10 to 0.90 are obtained depending on the speed selected: 10, 15 or 30 characters per second (density-meter GAM RD 144 with Wratten filter No. 106). The reaction threshold of these papers is at around 85° C.

In addition, for all the compositions of the examples, the behaviour under the effect of humidity is good; in fact, after storing thermally recorded images at 75% relative humidity and 23° C. for three months, the loss of density is less than 3%.

The properties of the papers mentioned in the above Examples are given in the Table hereinafter.

In this Table,

DO signifies: measured density of the non-recorded support,

D$_{max}$ signifies: measured density of the print.

The accelerated ageing tests were run with an apparatus known under the name of "SUNTEST 7011" manufactured by the firm HANAU under identical conditions as given in Example 3.

| EXAMPLE n° | COLOUR FORMER | DEVELOPER | Do | Dmax | THRESHOLD | COLOUR | SUNTEST HANAU T° + 30 hours | |
|---|---|---|---|---|---|---|---|---|
| | | | | | | | Do' | Dmax' |
| 1 | Crystal Violet lactone | Benzotriazole | 0.090 | 1.10 | 85° C. | blue | 0.090 | 0.25 |
| 2 | Black Pergascript IBR | Benzotriazole | 0.080 | 1.15 | 95° C. | black | 0.125 | 0.915 |

-continued

| EXAMPLE n° | COLOUR FORMER | DEVELOPER | Do | Dmax | THRESHOLD | COLOUR | SUNTEST HANAU T° + 30 hours | |
|---|---|---|---|---|---|---|---|---|
| | | | | | | | Do' | Dmax' |
| 3 | Black Pergascript IBR | Benzotriazole ZnCl₂ | 0.080 | 1.25 | 95° C. | black | 0.120 | 1.15 |
| 4 | Black Pergascript IBR | Benzotriazole ZnCl₂ | 0.080 | 1.20 | 85° C. | black | 0.120 | 1.10 |
| 5 | Black Pergascript IBR | Benzotriazole ZnCl₂ | 0.080 | 1.20 | 75° C. | black | 0.120 | 1.10 |
| 6 | Crystal Violet lactone | Benzotriazole ZnCl₂ | 0.085 | 1.15 | 85° C. | blue | 0.090 | 0.45 |
| 7 | Product T | Benzotriazole Mn(NO₃)₂ | 0.090 | 0.90 | 110° C. | reddish brown | 0.095 | 0.65 |
| 8 | Black Pergascript I6-B | Benzotriazole CuSO₄ | 0.090 | 1.40 (Wratten filter 581) | 80° C. | red | 0.120 | 1.20 |
| 9 | Black Pergascript IBR | Methyl-6 Benzotriazole ZnCl₂ | 0.080 | 1.20 | 75° C. | black | 0.120 | 1.10 |
| 10 | Copikem XI | Chloro-5 Benzotriazole ZnCl₂ | 0.090 | 1.40 (Wratten filter n° 47) | 95° C. | Orangey-yellow | 0.130 | 0.65 |
| 11 | Olive Pergascript I.G | Dimethyl-5,6 benzotriazole-1H monohydrate ZnCl₂ | 0.090 | 1.20 | 85° C. | Olive-green | 0.090 | 0.50 |
| 12 | Black Pergascript IBR | Nitro-5 Benzotriazole ZnCl₂ | 0.080 | 1.20 | 85° C. | Black | 0.120 | 1.10 |

What is claimed is:

1. A thermographic composition comprising a color former and a color developer, wherein said color developer comprises a compound of the formula:

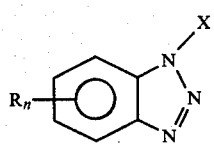

wherein R is selected from the group consisting of H, alkyl, NO₂, halogen, aryl, NH₂, OH, COOH, HSO₃, NR₁R₂, COOR₃, and OR₄, wherein R₁, R₂, R₃, and R₄ are selected from the group consisting of alkyl and aryl, wherein n is an integer of from 0 to 4, and wherein X is selected from the group consisting of H, a group possessing a labile H capable of forming a stable anion by loss of a proton H⁺, and their salts of formula, when X is H:

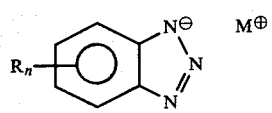

in which M⁺ represents a metal cation.

2. A thermographic composition according to claim 1, wherein X is selected from the group consisting of H, —OH, (CH₂)$_m$—OH in which m is an integer of from 1 to 10, and

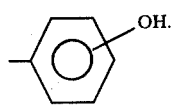

3. A thermographic composition according to claim 1 or 2, wherein X is H.

4. A thermographic composition according to claims 1 or 2, wherein the color developer is selected from the group consisting of benzotriazole, methyl-6-benzotriazole, chloro-5-benzotriazole, and dimethyl-5,6-benzotriazole-1H-monohydrate.

5. A thermographic composition according to claim 1, wherein R is selected from the group consisting of H, lower alkyl, halogen, and nitro.

6. A thermographic composition according to claim 1, wherein M is selected from the group consisting of Cu, Cd, Co, Fe (II), Ni, Mn and Zn.

7. A thermographic composition according to claim 1, wherein the color former is selected from the group consisting of triphenyl methane colorant lactones, fluorans, phthalides, triaryl methane leuco-colorants, spiropyrans, chromenes, chromanes, substituted phenothiazine or phenoxazine leuco-colorants.

8. A thermographic composition according to claims 1 or 7, further comprising at least one additional component selected from the group consisting of a polymer binder, waxes or compounds with low melting point, a pigmentary filler, and conventional additives.

9. A thermographic composition according to claims 1 or 7, wherein the color former/developer couples are selected from the group consisting of crystal violet lactone/benzotriazole, black color former/benzotriazole, product T/benzotriazole, wherein the product T corresponds to formula:

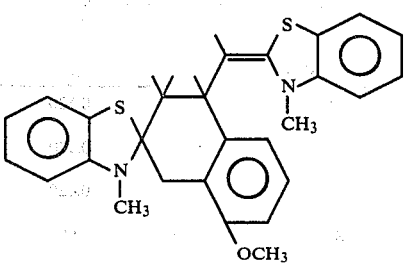

red color former/benzotriazole, black color former/-methyl-6-benzotriazole, color former "COPIKEM XI"/Cl-5-benzotriazole, olive color former/dimethyl-5,6-benzotriazole-1H-monohydrate, and black color former/nitro-5-benzotriazole.

10. A method for providing a thermographic recorded image comprising heating a thermographic composition to a temperature sufficient to cause a color forming reaction between a color former and color developer therein, wherein said color developer comprises a compound of the formula:

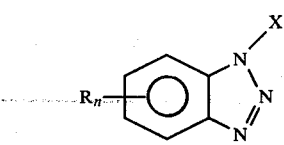

wherein R is selected from the group consisting of H, alkyl, $NO_2$, halogen, aryl, $NH_2$, OH, COOH, $HSO_3$, $NR_1R_2$, $COOR_3$, and $OR_4$, wherein $R_1$, $R_2$, $R_3$, and $R_4$ are selected from the group consisting of alkyl and aryl, wherein n is an integer of from 0 to 4, and wherein X is selected from the group consisting of H, a group possessing a labile H capable of forming a stable anion by loss of a proton $H^+$, and their salts of formula, when X is H:

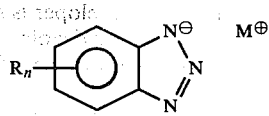

in which $M^+$ represents a metal cation.

11. A process according to claim 10, wherein X is selected from the group consisting of H, —OH, $(CH_2)_m$—OH in which m is an integer of from 1 to 10, and

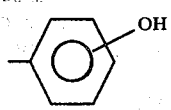

12. A process according to claim 10 or 11, wherein X is H.

13. A process according to claim 10 or 11, wherein the color developer is selected from the group consisting of benzotriazole, methyl-6-benzotriazole, chloro-5-benzotriazole, and dimethyl-5,6-benzotriazole-1H-monohydrate.

14. A process according to claim 10, wherein R is selected from the group consisting of H, lower alkyl, halogen, and nitro.

15. A process according to claim 10, wherein M is selected from the group consisting of Cu, Cd, Co, Fe (II), Ni, Mn and Zn.

16. A process according to claim 10, wherein the color former is selected from the group consisting of triphenyl methane colorant lactones, fluorans, phthalides, triaryl methane leuco-colorants, spiropyrans, chromenes, chromanes, substituted phenothiazine or phenoxazine leuco-colorants.

17. A process according to claim 10 or 16, wherein the thermographic composition further comprises at least one additional component selected from the group consisting of a polymer binder, waxes or compounds with low melting point, a pigmentary filler, and conventional additives.

18. A process according to claim 10 or 16, wherein the color former/developer couples are selected from the group consisting of crystal violet lactone/benzotriazole, black color former/benzotriazole, product T/benzotrriazole, wherein the product T corresponds to formula:

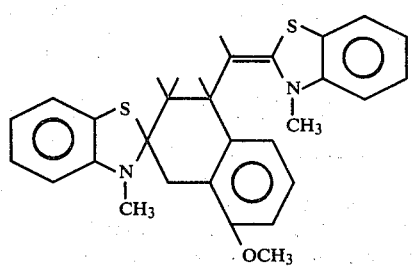

red color former/benzotriazole, black color former/-methyl-6-benzotriazole, color former "COPIKEM XI"/Cl-5-benzotriazole, olive color former/dimethyl-5,6-benzotriazole-1H-monohydrate, and black color former/nitro-5-benzotriazole.

19. A thermographic composition comprising a color former and a color developer, wherein said color developer comprises a compound of the formula:

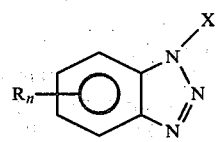

wherein R is selected from the group consisting of H, alkyl, $NO_2$, halogen, aryl, $NH_2$, OH, COOH, $HSO_3$, $NR_1R_2$, $COOR_3$, and $OR_4$, wherein $R_1$, $R_2$, $R_3$, and $R_4$ are selected from the group consisting of alkyl and aryl, wherein n is an integer of from 0 to 4, and wherein X is selected from the group consisting of H and the salts of formula:

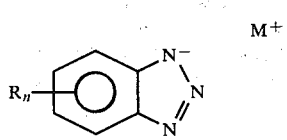

in which $M^+$ represents a metal cation.

20. A thermographic composition according to claim 19, wherein the color developer is selected from the group consisting of benzotriazole, methyl-6-benzotriazole, chloro-5-benzotriazole, and dimethyl-5,6-benzotriazole-1H -monohydrate.

21. A thermographic composition according to claim 19, wherein the color former/developer couples are selected from the group consisting of crystal violet lactone/benzotriazole, black color former/benzotriazole, product T/benzotriazole, wherein the product T corresponds to formula:

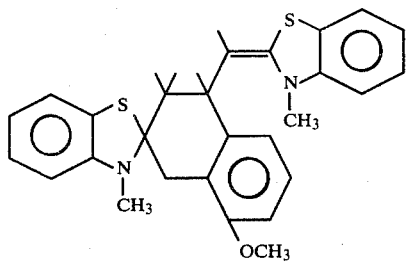

red color former/benzotriazole, black color former/methyl-6-benzotriazole, color former "COPIKEM XI"/chloro-5-benzotriazole, olive color former/dimethyl-5,6-benzotriazole-1H-monohydrate, and black color former/nitro-5-benzotriazole.

22. A method for providing a thermographic recorded image comprising the steps of heating a thermographic composition to a temperature sufficient to cause a color forming reaction between a color former and color developer therein, wherein said color developer comprises a compound of the formula:

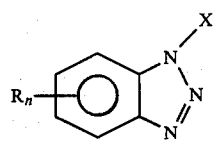

wherein R is selected from the group consisting of H, alkyl, $NO_2$, halogen, aryl, $NH_2$, OH, COOH, $HSO_3$, $NR_1R_2$, $COOR_3$, and $OR_4$, wherein $R_1$, $R_2$, $R_3$, and $R_4$ are selected from the group consisting of alkyl and aryl, wherein n is an integer of from 0 to 4, and wherein X is selected from the group consisting of H and the salts of formula:

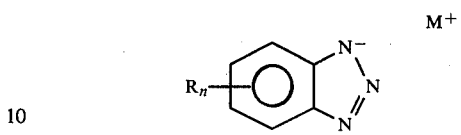

in which $M^+$ represents a metal cation.

23. A process according to claim 22, wherein the color developer is selected from the group consisting of benzotriazole, methyl-6-benzotriazole, chloro-5-benzotriazole, and dimethyl-5,6-benzotriazole-1H-monohydrate.

24. A process according to claim 22, wherein the color former/developer couples are selected from the group consisting of crystal violet lactone/benzotriazole, black color former/benzotriazole, product T/benzotriazole, wherein the product T corresponds to formula:

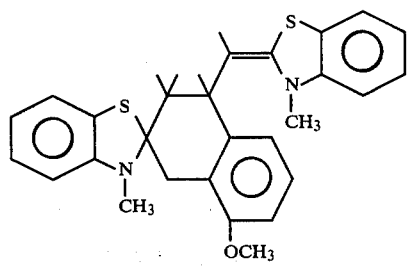

red color former/benzotriazole, black color former/methyl-6-benzotriazole, color former "COPIKEM XI"/chloro-5-benzotriazole, olive color former/dimethyl-5,6-benzotriazole-1H-monohydrate, and black color former/nitro-5-benzotriazole.

* * * * *

UNITED STATES PATENT AND TRADEMARK OFFICE
CERTIFICATE OF CORRECTION

PATENT NO. : 4,482,378
DATED : November 13, 1984
INVENTOR(S) : Riou et al.

It is certified that error appears in the above-identified patent and that said Letters Patent are hereby corrected as shown below:

Column 2, line 12, "product" should read --protect--.
Column 7, line 43, add ")" after "Chemicals" insert --)--.
Column 8, line 27, after "SEPPIC" insert --)--.
Column 11, line 24, after "agent" insert --of--.
Column 12, line 62, "T°" should read --$T_o$--.
Column 14, line 3, "T°" should read --$T_o$--.

Signed and Sealed this

Twenty-first Day of May 1985

[SEAL]

Attest:

DONALD J. QUIGG

Attesting Officer      Acting Commissioner of Patents and Trademarks